United States Patent [19]

Shaw et al.

[11] Patent Number: 5,196,198
[45] Date of Patent: Mar. 23, 1993

[54] PARENTERAL NUTRITION PRODUCT

[75] Inventors: Howard L. Shaw, Deerfield; William D. Leathem, Lindenhurst, both of Ill.

[73] Assignee: Abbott Laboratories, Abbott Park, Ill.

[21] Appl. No.: 899,821

[22] Filed: Jun. 16, 1992

Related U.S. Application Data

[63] Continuation of Ser. No. 458,858, Dec. 29, 1989, abandoned, which is a continuation-in-part of Ser. No. 360,966, Jun. 2, 1989, abandoned.

[51] Int. Cl.$^5$ .................... A61K 37/78; A61K 31/20
[52] U.S. Cl. .................. 424/195.1; 514/560; 514/549; 514/552; 514/558
[58] Field of Search .............. 424/195.1; 514/560, 514/549, 552, 558

[56] References Cited

U.S. PATENT DOCUMENTS

| 4,526,793 | 7/1985 | Ingenbleek | 426/72 |
| 4,703,060 | 10/1987 | Traitler | 514/549 |
| 4,753,963 | 6/1988 | Jandacek | 514/552 |

FOREIGN PATENT DOCUMENTS

| 2749492A | 1/1977 | Fed. Rep. of Germany. |
| 1580444 | 5/1977 | United Kingdom. |
| 2084172A | 8/1981 | United Kingdom. |

OTHER PUBLICATIONS

European Search Report of EP 90 11 0103.

Primary Examiner—David M. Naff
Assistant Examiner—Jean C. Witz
Attorney, Agent, or Firm—Dressler, Goldsmith, Shore, Sutker & Milnamow, Ltd.

[57] ABSTRACT

Parenteral nutritional compositions are described that contain a source of gamma-linolenic acid. A method of parenterally administering these compositions is also disclosed.

6 Claims, No Drawings

PARENTERAL NUTRITION PRODUCT

This application is a continuation of application Ser. No. 07/458,858, filed Dec. 29, 1989, abandoned, which is a continuation in part of application Ser. No. 07/360,966, filed Jun. 2, 1989, abandoned.

FIELD OF THE INVENTION

The present invention relates to a composition and method for the parenteral administration of fatty acids. More particularly, this invention relates to gamma-linolenic acid containing lipid emulsions for parenteral administration.

BACKGROUND OF THE INVENTION

Commercially available parenteral fat emulsions contain linoleic acid (18:2w6) as the principal fatty acid. Linoleic acid is converted to gamma-linolenic acid (18:3w6) with the aid of the enzyme, delta-6-desaturase. Gamma-linolenic acid is relatively rare in the human diet. Gamma-linolenic acid is found in human milk and in some oils such as borage oil. The conversion of linoleic acid to gamma-linolenic acid is the rate limiting step in the preparation of arachidonic acid and the prostaglandins, prostacyclin, PGE$_2$ and thromboxane. Synthesis of prostacyclin and PGE$_2$ is very desirable because they have a range of cytoprotective, antiaggretory, bronchodilation, vasodilation and anti-inflammatory properties.

Under certain conditions delta-6-desaturase is slow, absent or non-functioning in mammals. If linoleic acid is the primary nutritional fatty acid source, elevated levels of linoleic acid and an associated deficit of gamma-linolenic acid and other prostaglandin precursors can result. For example, gamma-linolenic acid production in neonates is low. Viral infections, saturated fats, aging, cancer, low zinc levels, alcohol, diabetes, Sjogren's syndrome and scleroderma also decrease the synthesis of gamma-linolenic acid and prostaglandins.

Thus, there is a need for a parenteral nutritional composition that avoids the effects of a deficit in the presence or function of delta-6-desaturase and increases the rate of formation of desirable prostaglandins.

SUMMARY OF THE INVENTION

The present invention relates to a parenteral nutritional composition that contains gamma-linolenic acid as a component with diminished levels of linoleic acid. More particularly, this invention relates to parenteral nutritional compositions that comprise from about 2 to about 30 weight percent fatty acids calculated as triglycerides, said fatty acids containing from about 1 to about 25 weight percent gamma-linolenic acid, and sufficient egg phosphatide, glycerin and water to prepare a lipid emulsion for parenteral administration. The compositions of the present invention can optionally contain fat soluble vitamins, as for example, vitamins A, D and E and L-carnitine. This invention also relates to a method of parenterally administering a therapeutically effective amount of a composition of the present invention to a mammal in need of such treatment.

DETAILED DESCRIPTION OF THE INVENTION

Presently preferred parenteral nutritional compositions contain borage oil as a source of gamma-linolenic acid. Borage oil is extracted by conventional techniques such as low temperature expeller pressing, direct solvent extraction or supercritical fluid extraction from the mature dried seeds of Borago officionale L., an herbaceous annual of the plant family Boraginaceae. Borage oil contains approximately 20 to 25 percent by weight of gamma-linolenic acid. The content of linoleic, gamma-linolenic and linolenic acids in borage oil, black currant seed oil, evening primrose oil and soybean oil is shown in TABLE 1.

TABLE 1

FATTY ACID COMPOSITION (%) OF GAMMA-LINOLENIC ACID CONTAINING SEED OILS

| FATTY ACIDS | BORAGE OIL | BLACK-CURRANT SEED | EVENING PRIMROSE OIL | SOY-BEAN OIL |
|---|---|---|---|---|
| Linoleic Acid 18:2w6 | 35–40 | 45–49 | 73–75 | 53–57 |
| Gamma-Linolenic Acid 18:3w6 | 21–25 | 15–19 | 7–10 | — |
| Linolenic Acid 18:3w3 | — | 13–15 | — | 7–9 |

The parenteral nutritional compositions of the present invention can contain from about 2 to about 30 weight percent fatty acids calculated as triglycerides. The fatty acids generally include a source of linoleic acid such as soybean or safflower oil, or mixtures thereof, and a source of gamma-linolenic acid such as borage oil. Soybean, safflower and borage oils are comprised of long chain triglycerides which contain fatty acids of 12 to 26 carbon atoms in length. In a preferred embodiment, borage oil is present in an amount sufficient to yield gamma-linolenic acid in an amount of from about 1 to about 25 weight percent of the total weight of fatty acids present in the composition. The nutritional composition can also contain medium chain fatty acids of 6 to 12 carbon atoms in length or mixtures thereof.

A parenteral nutritional composition of the present invention can comprise the following amounts of the below enumerated ingredients:

| Ingredient | Weight Percent |
|---|---|
| Soybean oil | 0–30 |
| Borage oil | 0.4–30.0 |
| (gamma-linolenic acid) | (0.1–7.5) |
| Egg phosphatide | 1–2 |
| Glycerin | 2–3 |
| Water | 56–87 |

The compositions of the present invention can also contain sufficient quantities of fat or water soluble vitamins to meet minimum daily requirements. For example, the compositions of the present invention can contain up to 2300 IU/day of Vitamin A for pediatric patients and up to 3300 IU/day of Vitamin A for adult patients, up to 400 IU/day of Vitamin D, up to 50 IU/day of Vitamin E and from 0.4–1.0 g/L-carotine/day. Other vitamins and minerals can be added in amounts sufficient to satisfy the daily requirements of adult, pediatric and neonatal patients.

The gamma-linolenic acid enriched parenteral nutritional formulations of the present invention can be used to treat patients with a variety of conditions where patients have a low level of delta-6-desaturase activity. For example, they may be used to treat:

1. neonates with immature enzyme systems;

2. patients with cystic fibrosis;
3. critically ill patients with acute respiratory distress syndrome and/or sepsis;
4. diabetics;
5. patients or alcoholics with hepatic dysfunction; and
6. patients recuperating from surgery or other acute trauma.

Other conditions that may be treated with gamma-linolenic acid enriched parenteral treatment formulations are cancer, acquired immune deficiency syndrome (AIDS), autoimmune disorders, hypermetabolic disorders and cardiovascular diseases.

Representative compositions of the present invention include the following:

| Gamma-Linolenic Acid Enriched Lipid Emulsion 20% | | | |
|---|---|---|---|
| Ingredient | 3% GLA | 5% GLA | 7% GLA |
| Soybean oil | 17.6 g | 16.0 g | 14.4 g |
| Borage oil | 2.4 g | 4.0 g | 5.6 g |
| (Gamma-linolenic acid) | (0.6 g) | (1.0 g) | (1.4 g) |
| Egg Phosphate | 1.2 g | 1.2 g | 1.2 g |
| Glycerin | 2.5 g | 2.5 g | 2.5 g |

In a treatment method of the present invention, compositions of the present invention are generally administered parenterally to patients in amounts sufficient to provide 0.02 to 4.0 g/kg/day of lipid. In a preferred embodiment, a formulation containing about 20 weight percent of a composition of the present invention is parenterally administered to a mammal or human patient.

The composition of the present invention may be prepared in accordance with known procedures in the art as illustrated by the following Examples which are not intended to limit the scope of the invention.

EXAMPLE 1

Water for injection (approximately 1 L) is heated and protected by a nitrogen atmosphere. Egg phosphatide (12 g) is added to approximately 600 ml of the water and dispersed by agitation at a temperature in the range of 50° to 90° C. Glycerin (25 g) is filtered through an 0.8 micrometer membrane filter and added to the dispersion. A Manton-Gaulin homogenizer is used to finely divide the egg phosphatide and increase the degree of dispersion. The aqueous phosphatide dispersion is then filtered through a nylon or equivalent membrane of 0.45 micrometer porosity and the pH is adjusted to a range of 8.5 to 10.5 with sodium hydroxide. Soybean oil, winterized (17.6 g) and borage oil, winterized (2.4 g) are filtered through a 0.45 micrometer membrane, heated to a temperature in the range of 55° to 95° C. and added to the egg phosphatide dispersion with agitation to form a coarse emulsion concentrate which is then homogenized using a Manton-Gaulin homogenizer at a pressure of 2000 to 8000 psi. The pH is then adjusted to a range of 8.5 to 9.5 if necessary with sodium hydroxide and the emulsion filtered through a nylon membrane of at least 0.8 micrometer porosity with sufficient surface area to provide minimum restriction of flow. The emulsion is then further homogenized in a Manton-Gaulin homogenizer, diluted to its desired concentration with sterile water and the pH adjusted to a range of 8.5 to 9.5 with sodium hydroxide.

EXAMPLE 2

Adult male Sprague-Dawley rats weighing 275±15 g were parenterally administered a 20% composition containing a 1:1 mixture of soybean and safflower oils or a lipid emulsion containing 3%, 5% or 7% by weight of gamma-linolenic acid (GLA). Control rats in each group were unstressed, while stressed rats received a thermal injury (immersion of shaved dorsal surface of rat in boiling water for 15 seconds) followed by an intraperitoneal, nonlethal 1 ml dose (0.5 mg/kg) of endotoxin (Salmonella enteriditis) in 0.9% saline, to induce sepsis.

All rats were fluid resuscitated with an intraperitoneal injection of sterile lactated Ringers solution (2.5 ml/100 g) followed by a four-hour intravenous infusion of 0.9% heparinized saline (10 U/ml) at a rate of 2.5 ml/hr.

Total intravenous nutrition was then delivered for three days through the left jugular vein. Each rat received 200 kcal/kg/day total calories, of which 40.2 kcal/kg/day were amino acids and 159.8 kcal/kg/day were non-protein calories (70% from dextrose and 30% from the lipid emulsion). After three days of total parenteral nutrition, the rats were sacrificed by exsanguination. Plasma samples were analyzed for total fatty acids present.

TABLE 2

| | | Total Plasma Fatty Acids (%) | | | | |
|---|---|---|---|---|---|---|
| Group | $N^1$ | Linoleic 18:2w6 | gamma-Linolenic 18:3w6 | DiHomo-gamma-Linolenic 20:3w6 | Arachidonic 20:4w6 | Linolenic 18:3w3 |
| Unstressed Rats[2] | | | | | | |
| soybean: safflower | 10 | 43.3 ± 2.1 | 0 | 0 | 19.7 ± 1.6 | 0.9 ± 0.3 |
| 3% GLA | 7 | 34.5 ± 0.7 | 0.5 ± .1 | 0.08 ± .08 | 22.7 ± 0.5 | 1.7 ± 0.1 |
| 5% GLA | 7 | 36.3 ± 1.3 | 1.1 ± .3 | 0.73 ± .2 | 20.7 ± 1.1 | 1.7 ± 0.4 |
| 7% GLA | 9 | 32.8 ± 1.3 | 1.8 ± .2 | 0.60 ± .2 | 22.9 ± 0.9 | 1.6 ± 0.1 |
| Stressed Rats[2] | | | | | | |
| soybean: safflower | 7 | 34.1 ± 2.2 | 0.09 ± .06 | 0.4 ± .24 | 27.7 ± 1.6 | 1.15 ± 0.2 |
| 3% GLA | 8 | 28.1 ± 1.2 | 0.35 ± .14 | 0.3 ± .14 | 30.7 ± 1.2 | 0.7 ± 0.3 |
| 5% GLA | 8 | 29.6 ± 1 | 1.3 ± .2 | 0.63 ± .14 | 30.7 ± 1.6 | 1.6 ± 0.1 |
| 7% GLA | 8 | 28.4 ± 1.1 | 1.7 ± .08 | 0.99 ± .06 | 29.8 ± 1.4 | 1.4 ± 0.1 |

[1] N = Number of animals
[2] Values = mean ± S.E.M.

EXAMPLE 3

Rats were maintained on total intravenous nutrition, as described in Example 2, and the isolated blood plasma was analyzed to determine the concentration of thromboxone $B_2$ (TXB2), 6-keto-prostaglandin $F_1$ alpha (KPGF), and bicyclic $PGE_2$ (BPGE) present.

The results are shown in TABLE 3.

TABLE 3

| Group | N[1] | Plasma Prostaglandin Concentration (PG/ml) | | | TXB2/KPGF |
| --- | --- | --- | --- | --- | --- |
| | | TXB2 | KPGF | BPGE | |
| Unstressed Rats[2] | | | | | |
| soybean: safflower | 10 | 1188 ± 225 | 190 ± 71 | 353 ± 22 | 11 ± 2 |
| 3% GLA | 7 | 1218 ± 291 | 135 ± 32 | 342 ± 37 | 14 ± 6 |
| 5% GLA | 7 | 1013 ± 254 | 311 ± 72 | 386 ± 57 | 5 ± 1 |
| 7% GLA | 9 | 828 ± 253 | 109 ± 22 | 311 ± 84 | 14 ± 7 |
| Stressed Rats[2] | | | | | |
| soybean: safflower | 7 | 1608 ± 231 | 213 ± 132 | 247 ± 25 | 24 ± 8 |
| 3% GLA | 8 | 1771 ± 199 | 320 ± 61 | 420 ± 99 | 7 ± 1 |
| 5% GLA | 8 | 1590 ± 175 | 543 ± 143 | 352 ± 42 | 8 ± 4 |
| 7% GLA | 8 | 1133 ± 211 | 208 ± 77 | 360 ± 75 | 11 ± 3 |

[1]N = Number of animals
[2]Values = mean ± S.E.M.

EXAMPLE 4

Rats maintained on total intravenous nutrition, as described in Example 2, were monitored for changes in body weight during the studies. The results are shown in Table 4.

TABLE 4

| Group | N[1] | Body Weight Change (grams) |
| --- | --- | --- |
| Unstressed Rats[2] | | |
| soybean: safflower | 10 | −7.0 ± 3.1 |
| 3% GLA | 7 | 0.3 ± 1.3 |
| 5% GLA | 8 | 2.2 ± 1.7 |
| 7% GLA | 9 | −2.7 ± 1.3 |
| Stressed Rats[2] | | |
| soybean: safflower | 7 | −14.5 ± 2.0 |
| 3% GLA | 8 | −7.2 ± 1.9 |
| 5% GLA | 8 | −13.8 ± 2.1 |
| 7% GLA | 8 | −11.1 ± 1.1 |

[1]N = Number of animals
[2]Values = mean ± S.E.M.

EXAMPLE 5

Rats maintained on total intravenous nutrition, as described in Example 2, were monitored for cumulative nitrogen balance by collecting 24-hour urine samples over the three-day period of intravenous nutrition. The nitrogen balance was determined as the difference between total urinary nitrogen and total dietary nitrogen intake (1.5 g of N/kg/day); the sum of the daily nitrogen balances was reported as the cumulative nitrogen balance.

The results are shown in TABLE 5.

TABLE 5

| Group | N[1] | Cumulative Nitrogen Balance (mg/day) |
| --- | --- | --- |
| Unstressed Rats[2] | | |
| soybean: safflower | 10 | 357 ± 34 |
| 3% GLA | 7 | 351 ± 44 |
| 5% GLA | 8 | 309 ± 46 |
| 7% GLA | 9 | 348 ± 31 |
| Stressed Rats[2] | | |
| soybean: safflower | 7 | −85 ± 41 |
| 3% GLA | 8 | −115 ± 28 |
| 5% GLA | 8 | −66 ± 30 |
| 7% GLA | 8 | −127 ± 17 |

[1]N = Number of animals
[2]Values = mean ± S.E.M.

The foregoing specification, including the specific embodiments and Examples, is intended to be illustrative of the present invention and is not to be taken as limiting. Numerous other variations and modifications can be made without departing from the true spirit and scope of the present invention.

What is claimed is:

1. A parenteral nutritional composition that contains fatty acids, wherein such fatty acids are present in an amount from about 2 to about 30 weight percent calculated as triglycerides where from about 1 to about 25 weight percent of said fatty acids is gamma-linolenic acid provided by an oil having a weight percent ratio of linoleic acid to gamma-linolenic acid less than 2 and where the weight percent ratio of gamma-linolenic acid to linoleic acid in said fatty acids is about 0.05 to about 1.50.

2. The composition according to claim 1 wherein the gamma-linolenic acid is derived from borage oil.

3. The composition according to claim 1 that further comprises fat soluble vitamins or L-carnitine.

4. A method of providing fatty acids to a mammal in need of fatty acids comprising parenterally administering to said mammal the composition according to claim 1.

5. A method of providing fatty acids to a mammal in need of fatty acids comprising parenterally administering to said mammal a therapeutically effective amount of a composition containing fatty acids, wherein such fatty acids are present in an amount from about 2 to about 30 weight percent calculated as triglycerides where from about 1 to about 25 weight percent of said fatty acids is gamma-linolenic acid provided by an oil having a weight percent ratio of linoleic acid to gamma-linolenic acid less than 2 and where the weight percent ratio of gamma-linolenic acid to linoleic acid in said fatty acids is from about 0.05 to about 1.50.

6. The method according to claim 5, wherein a formulation comprising about 20 percent by weight of said composition is administered to said mammal.

* * * * *

UNITED STATES PATENT AND TRADEMARK OFFICE
CERTIFICATE OF CORRECTION

PATENT NO. : 5,196,198

DATED : March 23, 1993

INVENTOR(S) : Shaw et al.

It is certified that error appears in the above-identified patent and that said Letters Patent is hereby corrected as shown below:

Column 2, Line 46   Under Weight Percent for Borage Oil, it should read -- 0.4-3.0 --.

Signed and Sealed this

Eighth Day of November, 1994

Attest:

BRUCE LEHMAN

*Attesting Officer*    *Commissioner of Patents and Trademarks*